United States Patent
Plasson et al.

(10) Patent No.: US 9,192,167 B2
(45) Date of Patent: Nov. 24, 2015

(54) METHOD FOR THE BIOLOGICAL CONTROL OF LISTERIA

(71) Applicant: AMOEBA, Lyons (FR)

(72) Inventors: Fabrice Plasson, Lyons (FR); Séléna Bodennec, Les Avenières (FR)

(73) Assignee: AMOEBA, Lyons (FR)

( * ) Notice: Subject to any disclaimer, the term of this patent is extended or adjusted under 35 U.S.C. 154(b) by 0 days.

(21) Appl. No.: 14/361,762

(22) PCT Filed: Dec. 3, 2012

(86) PCT No.: PCT/EP2012/074248
§ 371 (c)(1),
(2) Date: Jul. 17, 2014

(87) PCT Pub. No.: WO2013/079722
PCT Pub. Date: Jun. 6, 2013

(65) Prior Publication Data
US 2014/0328800 A1 Nov. 6, 2014

(30) Foreign Application Priority Data
Dec. 2, 2011 (FR) .................... 11 61111

(51) Int. Cl.
| | |
|---|---|
| *A01N 63/02* | (2006.01) |
| *C12R 1/90* | (2006.01) |
| *A01N 63/00* | (2006.01) |
| *C02F 3/32* | (2006.01) |
| *C02F 103/02* | (2006.01) |

(52) U.S. Cl.
CPC ............... *A01N 63/02* (2013.01); *A01N 63/00* (2013.01); *C12R 1/90* (2013.01); *C02F 3/327* (2013.01); *C02F 2103/023* (2013.01)

(58) Field of Classification Search
None
See application file for complete search history.

(56) References Cited

U.S. PATENT DOCUMENTS 8,168,167 B2 * 5/2012 Bodennec et al. ........... 424/93.1

FOREIGN PATENT DOCUMENTS

WO   WO 2008/043969   4/2008

OTHER PUBLICATIONS

Akya et al., "Viability of *Listeria monocytogenes* in co-culture with *acanthamoeba spp*," FEMS Microbiology Ecology, vol. 70, No. 1, Oct. 2009, pp. 20-29.

Dey et al., "Free-living fresh water amoebae differ in their susceptibility to the pathogenic bacterium *Legionella pnuemophila*," FEMS Microbiology Letters, vol. 290, No. 1, Jan. 2009, pp. 10-17.

* cited by examiner

*Primary Examiner* — Blaine Lankford
*Assistant Examiner* — David Berke-Schlessel
(74) *Attorney, Agent, or Firm* — Fanelli Haag PLLC

(57) ABSTRACT

The invention relates to a method for controlling the proliferation of *Listeria*, with the exception of the treatment methods applied to the human or animal body, characterized in that it uses protozoa of the *Willaertia magna* species, and also to a disinfecting agent containing such protozoa.

5 Claims, 3 Drawing Sheets

METHOD FOR THE BIOLOGICAL CONTROL OF LISTERIA

Figure 1:
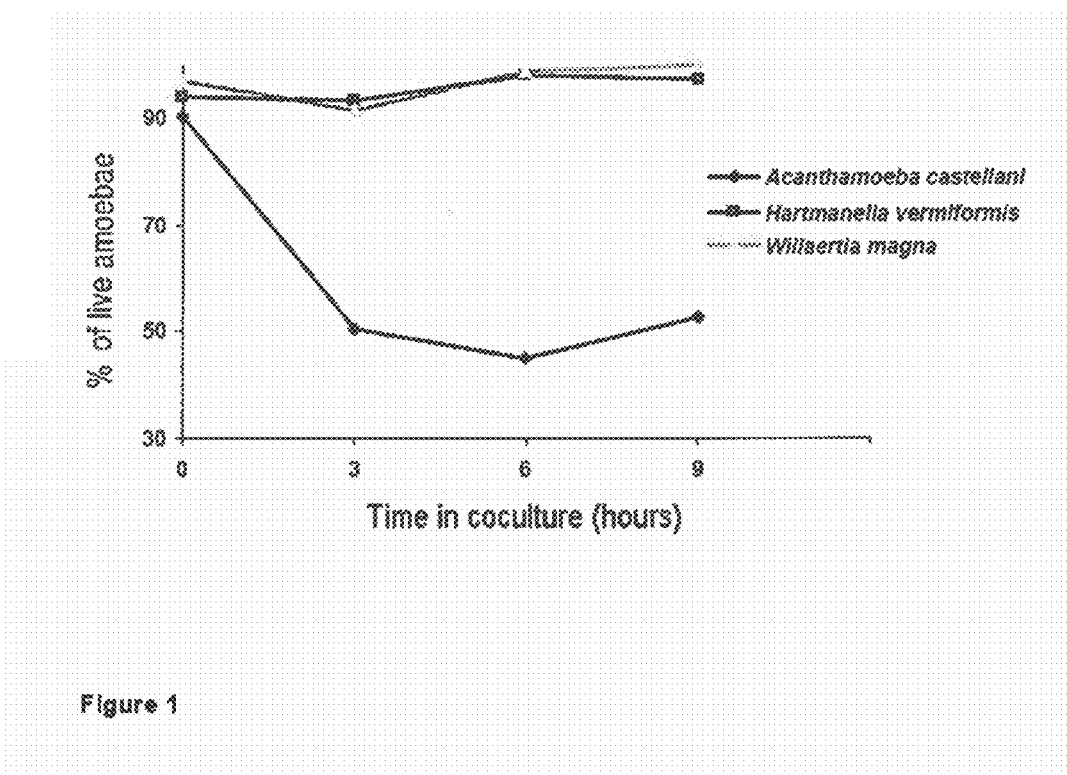

This application is a U.S. National Stage Application of PCT International Patent Application No. PCT/EP2012/074248, which was filed on Dec. 3, 2012 which claims priority to French Patent Application No. 1161111 filed Dec. 2, 2011, the disclosure of each of which is incorporated herein by reference in its entirety.

The present invention relates to a novel method for the biological control of *Listeria* and in particular *Listeria monocytogenes*, and also to a novel composition intended for controlling the proliferation of *Listeria monocytogenes*.

*Listeria monocytogenes* is a Grain-positive bacterium belonging to the family Listeriaceae. In humans, this bacterium is responsible for listeriosis with a prognosis that is often fatal (10). In survivors, serious after-effects are often observed. The pathogenic bacterium can cross the intestinal barrier and the placental barrier, then being able to cause infections of the fetus or of the newborn, or premature births. *Listeria monocytogenes* is also a major cause of neuroinvasive infection with an increasing prevalence over the past few years (5) (10). Thus, the monitoring and the prevention of listeriosis constitute an increasingly important preoccupation.

*Listeria monocytogenes* is a bacterium with ubiquitous dissemination/distribution: it is present in soil, water, as an epiphyte on plants, etc. Very resistant to cleaning-disinfection treatments, it can thus persist in production units of the food-processing industry, for example, or air-conditioning or water distribution networks for example.

Generally, and despite the medical significance of this bacterium, knowledge regarding the ecology of *Listeria* remains relatively limited (1). However, it is known that, in the environment, *Listeria monocytogenes* has a ubiquitous distribution (15), since this bacterium has been isolated from the soil, from sewage or from industrial wastewater (4), a characteristic that it shares with free-living amoebae. Furthermore, the capacity of *Listeria monocytogenes* to resist destruction by human macrophages has enabled certain scientists to put forward the hypothesis that this pathogenic bacterium could resist free-living amoebae in the environment, by analogy with the knowledge acquired regarding relationships between parasitic bacteria and amoebic hosts (6). Thus, Ly and Müller have suggested that *Listeria* could be resistant to free-living amoebae (6, 9). These hypotheses could be verified when these authors demonstrated that *Listeria monocytogenes* was capable of proliferating in the presence of free-living amoebae belonging to the *Acanthamoeba* genus (9) (6). Furthermore, a cytotoxic effect of *Listeria monocytogenes* on amoebic hosts has been demonstrated, since encystment of *Acanthamoeba* is observed when the latter are placed in coculture with the pathogenic bacterium (6, 9). Zhou et al have also been able to show that *Listeria monocytogenes* has the ability to resist free-living *Acanthamoeba castellanii* amoebae (16). It has also been demonstrated that *Listeria monocytogenes* is capable of growing in the presence of biological material released by amoebae during encystation thereof or lysis thereof (1). The authors of this observation had suggested that these factors could provide *Listeria* with favorable conditions for the maintenance and/or proliferation thereof in the environment (1). Other observations carried out by Pushkareva and Ermolaeva have made it possible to demonstrate, in another free-living protozoan (*Tetrahymena pyriformis*), that *Listeria monocytogenes* is actually internalized (11). The infestation of *Tetrahymena pyriformis* by *Listeria monocytogenes* induces encystment of the protozoan (11). The data obtained by these researchers have also shown that the *Listeria monocytogenes* internalized in these protozoan cysts remain viable, retain their virulence and are capable of causing infections in animal models (11).

It therefore clearly appears that free-living protozoa and amoebae constitute an important element of the ecology of *Listeria monocytogenes*, by promoting maintenance thereof and growth thereof in the environment and by promoting the emergence of bacterial virulence traits. Furthermore, the capacity of *Listeria* to infect protozoa and to survive in their cystic forms (11) is a powerful indicator that protozoa are factors which promote the resistance of *Listeria* to the biocidal treatments currently used. Amoebic cysts in fact exhibit a very great resistance to the chemical and/or physical biocidal treatments currently used (7, 8, 14). The biocidal treatments currently used for preventing *Listeria* risk are not satisfactory since, in addition to the development of resistances intrinsic to the bacterium per se (12, 13), the bacteria present inside protozoa and in biofilms (2) are relatively protected, and will therefore continue to proliferate/colonize their environment.

In this context, the inventors have demonstrated, totally unexpectedly, that the amoebic genus *Willaertia magna* eradicates *Listeria monocytogenes* bacteria. This biocidal effect is added to by the already demonstrated capacity of *Willaertia magna* for predation toward other amoebic agents that may serve as a vector for *Listeria monocytogenes* (3).

A subject of the present invention is therefore first of all a method for controlling the proliferation of *Listeria*, and in particular *Listeria monocytogenes*, which uses protozoa of the *Willaertia magna* genus. The methods in accordance with the invention do not include the treatment methods applied to the human or animal body. In the method according to the invention, it is most commonly a gas or liquid stream which is treated with protozoa of the *Willaertia magna* genus and in particular the *Willaertia magna* species.

For the purposes of the invention, the term "*Listeria*" is intended to mean any species of *Listeria* and in particular *Listeria monocytogenes*.

The method according to the invention can in particular be used in the disinfection of sanitation water or industrial water distribution networks, cooling circuits for industrial plants, or air-conditioning networks, or as a surface disinfectant. The protozoa may be directly added to the water or liquids circulating in the pipes or networks to be treated. It is also possible to spray them, for example in the form of an aqueous solution as an aerosol, in the industrial networks, chimneys and plants, and on the industrial surfaces, to be disinfected.

Advantageously, the protozoa used in the context of the invention correspond to the strain deposited on Aug. 26, 2006, under number PTA 7824 at the ATCC, or to the strain deposited on Aug. 26, 2006, under number PTA 7825 at the ATCC, these two strains having been deposited in the names of the Centre National de la Recherche Scientifique (CNRS) [French National Center for Scientific Research]-3 rue Michel Ange-75794 Paris Cedex 16/France-and the Université Lyon 1 Claude Bernard [Lyon 1 Claude Bernard University]-Boulevard du 11 Novembre 1918-69622 Villeurbanne Cedex/France.

The protozoa belonging to the *Willaertia* genus corresponding to the strain deposited under number PTA 7824 at the ATCC or to the strain deposited under number PTA 7825 at the ATCC are an integral part of the invention. Said deposited strains PTA 7824 and PTA 7825 are also described in the publication of PCI International application WO 2008/043969.

Such protozoa may therefore be used in disinfecting agents, in particular intended for eliminating *Listeria* and in particular *Listeria monocytogenes* bacteria and for controlling the proliferation and contamination by listeriosis.

A subject of the invention, according to another of its aspects, is a disinfecting agent containing protozoa of the *Willaertia* genus, and in particular of the *Willaertia magna* species. The protozoa corresponding to the strain deposited under number PTA 7824 at the ATCC or to the strain deposited under number PTA 7825 at the ATCC will be preferred. Advantageously, the disinfecting agent according to the invention is in the form of an aqueous solution or suspension, for example in distilled water. The disinfecting agent may be in a sprayable form, for example as an aerosol or any other means of application.

The *Listeria monocytogenes* proliferation-inhibiting activity of the protozoa of the *Willaertia* genus, and in particular of the *Willaertia magna* species, has been demonstrated by the inventors by comparing the replication of *Listeria monocytogenes* in the *Acanthamoeba* and *Hartmannella* genera used as amoebic models, with that observed in the *Willaertia* amoebic genus.

Given the essential role played by amoebae in the proliferation and maintenance of *Listeria* and in particular *Listeria monocytogenes* in the external environment, elements which condition the epidemiology of listeriosis since there is no inter-human transmission, the method and the disinfecting agent according to the invention have numerous advantages, in terms of cost, of effectiveness and of environmental friendliness, in particular.

The examples hereinafter make it possible to illustrate the invention but have no limiting nature.

FIG. 1 shows the spontaneous evolution of the respective populations of *Hartmannella, Acanthamoeba* and *Willaertia* amoebae after placing in coculture with *Listeria monocytogenes* at an initial amoeba/bacterium ratio of 10.

The various free-living amoebae are placed in coculture (time 0 hour) with *Listeria monocytogenes* at a ratio of 10 (10 bacteria/1 amoeba) as described in the materials and methods section. Aliquots of the cell suspensions are then taken every 3 hours following the placing in coculture, and the percentage of live amoebae is determined by means of a trypan blue exclusion test and microscopic observation using a Malassez cell. The data are expressed as % of live cells, negative in the trypan blue exclusion test.

FIG. 2 shows the compared kinetics of the development of *Listeria monocytogenes* obtained in coculture with various amoebic genera, including the *Willaertia* genus.

The various free-living amoebae are separately placed in cocultures (time 0 hour) with *Listeria monocytogenes* at a ratio of 10 (10 bacteria/1 amoeba). Aliquots of the cell suspensions are then taken every 3 hours following the placing in coculture, and the *Listeria monocytogenes* concentrations are determined as described in the materials and methods section.

FIG. 3 shows the biocidal effect of *Willaertia magna* on a biofilm formed by *Listeria monocytogenes*. This figure also shows the absence of effect of the free-living *Acanthameoba castellanii* and *Hartmanella vermiformis* amoebae.

The *Listeria monocytogenes* were inoculated onto TSA agar, which is incubated at 30° C. for 48 hours in order to ensure the formation of a dense biofilm of bacteria on the agar. Then, $1\times10^5$ amoebae (*Acanthamoeba castellanii*, panel A; *Hartmanella vermiformis*, panel B; *Willaertia magna*, panels C and D) resuspended in 100 μl of sterile deionized water are inoculated at the center of the agar. After 24 hours at 30° C., the agars are examined under a microscope in order to determine the appearance of the amoebae and the influence of the latter on the biofilm. A: The white arrows show the appearance of the groups of cysts formed by *Acanthamoeba castellanii* in the presence of *Listeria monocytogenes* (L. m.). The absence of bacterial layer lysis plaque around the groups of amoebic cysts should be noted. B: Note the presence of numerous cystic forms of *Hartmanella vermiformis*, some examples of which are indicated by white arrows. Also note the very high density of *Listeria monocytogenes* surrounding the *Hartmanella vermiformis* cysts and the total absence of bacterial biofilm lysis plaques, C: Effect of the *Willaertia magna* on the biofilm formed by *Listeria monocytogenes*. The white arrows indicate groups of *Willaertia magna* trophozoites located at the front of a biofilm lysis plaque. Note the absence of bacterial film (zone delimited by the white circle in the bottom left comet of the photomicrograph) upstream of the groups of *Willaertia magna* and the dense bacterial film (indicated by the initials L. m.) downstream of the groups of amoebae (top right corner of the photomicrograph). D: another photomicrograph showing the formation of lysis plaques of the biofilm formed by *Listeria monocytogenes*. Note the groups of *Willaertia magna* and the bacterial biofilm lysis plaque fronts (indicated by the white points).

I. MATERIALS AND METHODS

1.1. Strains Used

*Listeria monocytogenes*: the strain used is the CL 3970 strain (Oxoid, France).

It is maintained on TSA (Tryptone Soya Agar) (ref PO 5012, Oxoid, France) at a rate of one subculturing per week. The strain is inoculated in broad streaks onto a TSA plate and incubated for 2 days at 30° C.

*Amoebae*: the strains used belong to three different amoebic species:

*Hartmannella vermiformis,*

*Acanthamoeba castellanii*, strains deposited at the ATCC under No. 30010,

*Willaertia magna* (strains deposited at the ATCC under Nos. PTA7824 and PTA 7825).

These three strains are cultured axenically, in the presence of 10% of fetal calf serum, on SCGYEM medium (Serum Casein Glucose Yeast Extract Medium), distributed into Falcon® tubes (3033) in a proportion of 3 ml per tube. In maintenance, the vegetative forms are subcultured every 8-9 days. For the cocultures, 3-to-4-day subcultures are used so as to have trophozoites right in the exponential growth phase.

The SCGYEM medium is obtained as follows:

| | |
|---|---|
| Casein (Merck 1.02244.010) | 10 g |
| $Na_2HPO_4$ | 1.325 g |
| $KH_2PO_4$ | 0.8 g |
| Glucose | 2.5 g |
| Yeast extract (Difco 0127-17-9) | 5 g |
| Distilled water | 900 ml |
| Fetal calf serum | 100 ml |

2.5 ml of NaOH (1N), then $Na_2HPO_4$ and $KH_2PO_4$, are added to 900 ml of distilled water. The mixture is heated slightly on a hotplate, and then the casein is gradually added with magnetic stirring. After the casein has dissolved, the glucose and the yeast extract are incorporated.

After complete dissolution, the mixture is filtered successively on glass fiber (Sartorius SM 6513400), and then on a 1 μm membrane (Whatman 7190 004). The medium is then aliquoted into glass bottles. The bottles are sterilized in an autoclave for 20 minutes at 120° C. Before the definitive use and distribution of the medium, the fetal calf serum is added sterilely, under a laminar flow hood, in a proportion of 10% of the final volume.

1.2 Monoamoebic Coculture of *Listeria Monocytogenes*

1.2.1 Preparation of the Bacterial Inoculum

A suspension of *Listeria monocytogenes* in sterile distilled water is prepared from a 2-day culture on TSA, so as to obtain 1 Optical Density unit at 550 nm, i.e. a concentration of $10^9$ CFU (colony-forming units)/ml.

1.2.2 Carrying Out Monoamoebic Cocultures

The cocultures are carried out in cell culture tubes (Falcon® 3033) containing 3 ml of autoclave-sterilized water. The inoculation of the tubes is carried out in a proportion of $1\times10^5$ amoebae/ml, from an axenic amoebic suspension canted beforehand on a Malassez hemocytometer. The infestation of the amoebae with *Listeria monocytogenes* is carried out by fixing a *Listeria monocytogenes*/amoeba ratio of 10, i.e. $1\times10^6$ bacteria/ml of incubation medium. Immediately after the infestation, the coculture tubes are centrifuged at low speed (760 g for 10 min) in order to promote contact between amoebae and bacteria. After 10 min, the tubes are resuspended manually and are incubated, in the inclined position, in an incubator at 30° C.

The fates of the amoebae and of *Listeria monocytogenes* placed in coculture are determined in the following way:

The cocultures are monitored for 9 hours after the bacterial infestation. At each time interval (every 3 hours), the coculture tubes are sampled and examined from both the amoebic point of view and the bacterial point of view after vigorous stirring on a vortex in order to detach the amoebae from the walls. For each tube examined:

The amoebae are counted directly on a Malassez cell.

The *Listeria monocytogenes* concentrations are determined by directly plating the culture medium out on TSA after 10-fold serial dilution in sterile distilled water, in Eppendorf microtubes. Each dilution is plated out in triplicate on ISA in a proportion of 100 µl per plate. The plates are then incubated at 30° C. for a minimum of 48 hours. A first reading of the TSAs is carried out 24 hours after the plating out, by counting the colonies; it is followed by a second reading on the 2nd day for confirmation. The *Listeria monocytogenes* concentrations are expressed in CFU/ml of incubation medium, taking into account the dilution factor and assuming that each colony corresponds to one bacterium initially present in the diluted suspension.

For each amoebic genus, the *Listeria monocytogenes* growth curves are represented as a function of time.

In addition, the possible cytotoxic effect of *Listeria monocytogenes* on the various amoebic species is determined in the following way:

by counting the proportion of amoebae which are positive in the trypan blue exclusion test. This test is carried out under a microscope by counting, in a Malassez cell, the number of trypan blue-positive cells/number of total cells;

by determining the propensity of the amoebae to become encysted in the presence of *Listeria monocytogenes*.

1.3. Effect of *Willaertia Magna* on *Listeria Monocytogenes* Biofilms

The *Listeria monocytogenes* biofilms are brined in the following way: a predetermined amount of *Listeria monocytogenes* in 100 µl of sterile water is deposited and plated out on a TSA. The agars are placed at 30° C. for 48 hours so as to allow the development of a dense and uniform bacterial film over the whole of the surface of the agar. Then, $1\times10^5$ amoebae (*Acanthamoeba castellanii, Hartmanella vermiformis* or *Willaertia magna*) are deposited at the center of the agar which is placed at 30° C. for 24 hours. The agars are then observed under an optical microscope (magnification×400) in order to detect therein the formation of possible bacterial layer lysis plaques.

2. RESULTS

2.1 *Willaertia Magna* Exhibits Resistance to *Listeria Monocytogenes*

The effect of *Listeria monocytogenes* on the survival of the various amoebic species tested was determined by means of a trypan blue exclusion test. Very rapidly, after placing *Acanthamoeba castellanii* in coculture with the bacterium, a major cytotoxic effect occurs in this amoebic species, with a drop of ~50% in the viability after 3 hours of coculture (see FIG. 1). Conversely, this phenomenon is never observed when *Willaertia magna* is placed in coculture with *Listeria monocytogenes*, including up to 9 hours of incubation with a viability which is maintained close to 100% (FIG. 1). Like *Willaertia magna*, the free-living *Hartmanella vermiformis* amoeba does not exhibit any drop in terms of viability determined by trypan blue exclusion (FIG. 1). However, microscopic examination of the amoebic-*Listeria monocytogenes* cocultures demonstrates a strong propensity for encystment in *Hartmanella vermiformis* and in the viable forms of *Acanthamoeba castellanii* (see table 1). This encystment phenomenon is never observed in *Willaertia magna* when placed in coculture with the pathogenic bacterium (table 1).

TABLE 1

Effect of *Listeria monocytogenes* on the induction of cystic forms in the various species of free-living amoebae

| | Time in coculture (hours) | | | |
| --- | --- | --- | --- | --- |
| | 0 | 3 | 6 | 9 |
| Harmanella vermiformis | ND | + | ++ | ++ |
| Acanthamoeba castellanii | ND | ND | + | +++ |
| Willaertia magna | ND | ND | ND | ND |

The free-living amoebae are placed in coculture (time 0 hour) with *Listeria monocytogenes* at a ratio of 10 (10 bacteria/1 amoeba) as described in the materials and methods section. Aliquots of the cell suspensions are then taken every 3 hours following the placing in coculture, as indicated in the table above. The amoebic cyst density is expressed in the following way:

ND: cysts not detected; +: presence of cysts (proportion less than 10% of the viable forms); ++: presence of cysts (proportion between 10% and 30% of the viable forms); +++: presence of cysts (proportion greater than 30% of the viable forms).

All of these observations (no encystment and no cytotoxicity induced by *Listeria monocytogenes*) clearly demonstrate that *Willaertia magna*, contrary to the other amoebic species, exhibits the initial ability to resist *Listeria monocytogenes*.

2.2. Predation of *Listeria Monocytogenes* by *Willaertia Magna*

Figure 2:
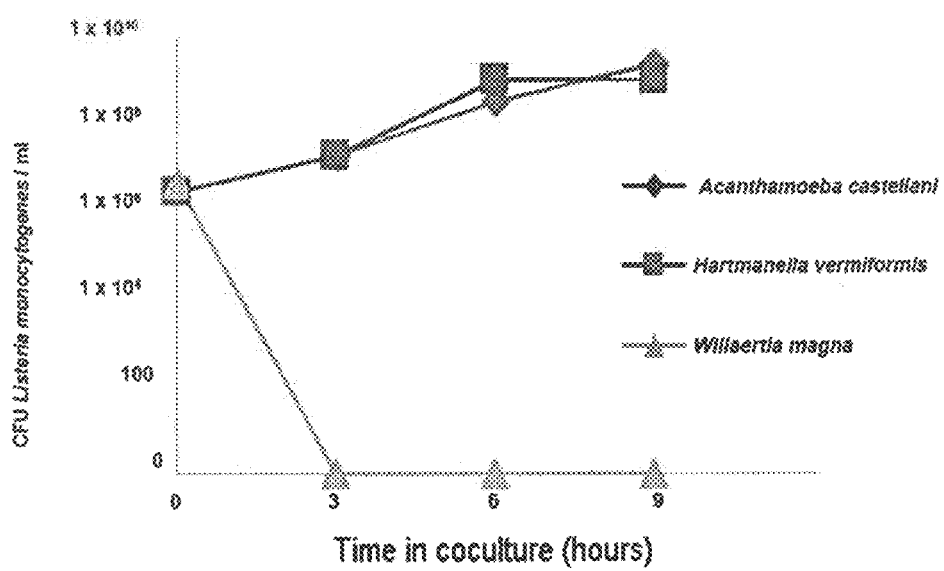

The results of the *Listeria monocytogenes* cocultures carried out in the presence of amoebae belonging to the *Hartmannella* and *Acanthamoeba* genera demonstrate a considerable multiplication of the bacterium in the presence of these two amoebic genera since an increase reaching ~3 log in the bacterial concentrations is noted in 9 hours (see FIG. 2). Conversely, although the cocultures are carried out under strictly identical conditions, a total disappearance of detectable *Listeria monocytogenes* is noted in the presence of the *Willaertia magna* amoeba (see FIG. 2). The drop in *Listeria monocytogenes* concentrations that is measured is ~6 Log in 3 hours, demonstrating a massive predation effect of *Willaertia magna* toward *Listeria monocytogenes*.

Figure 3:
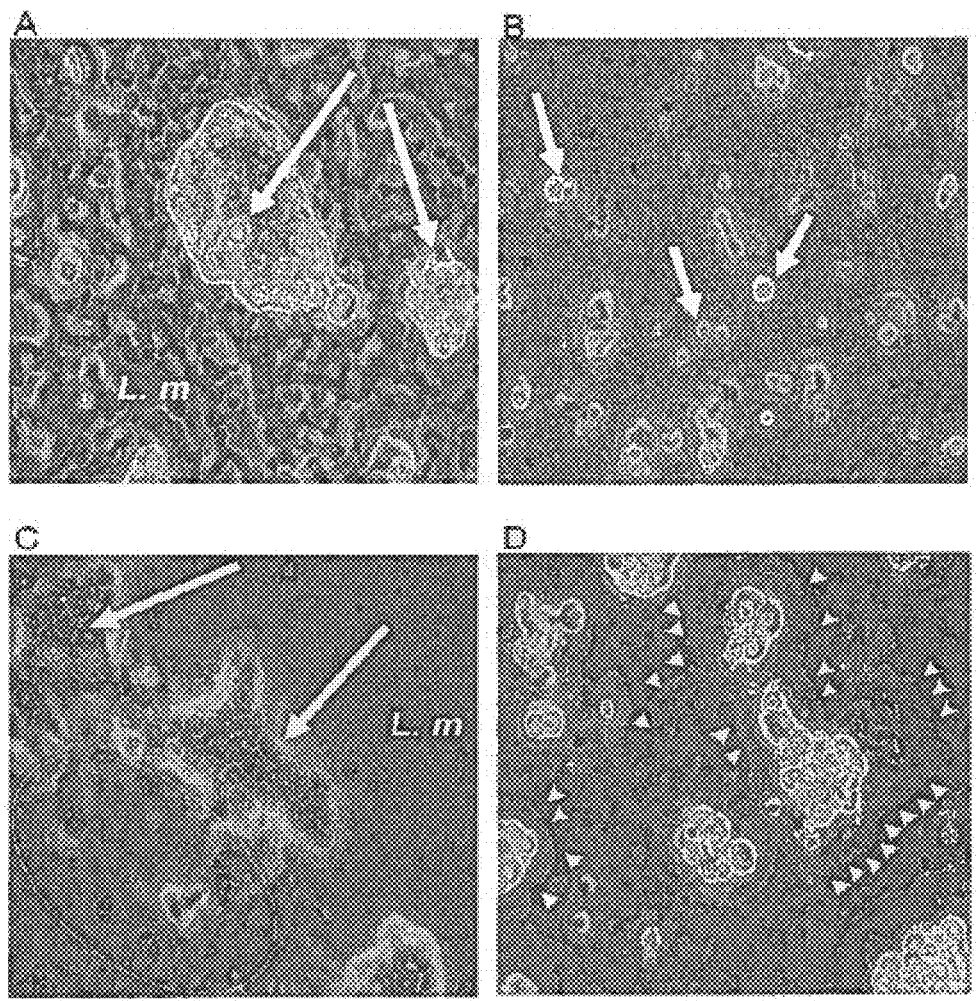

This effect of *Willaertia magna* on *Listeria monocytogenes* is further illustrated in FIG. 3. Thus, after 24 hours in the presence of *Willaertia magna*, surfaces of the agar where the bacterial layer has disappeared appear very clearly (these zones are referred to here as bacterial layer/biofilm lysis plaques). The microscopic examination also shows that the *Willaertia magna* are concentrated at the limit of this lysis plaque; this effect is illustrated in FIG. 3, panel C. The destruction of the bacterial layer by *Willaertia magna* is also illustrated in panel D of FIG. 3, where groups of amoebae surrounded by a bacterial layer which has been destroyed or is in the process of being destroyed are clearly distinguished. Conversely, in the presence of *Acanthamoeba castellanii* or of *Hartmanella vermiformis*, it was never possible to observe this phenomenon. The microscopic examination of the agars shows that the *Acanthamoeba castellanii* and *Hartmanella vermiformis* amoebae encyst rapidly when deposited on the film of *Listeria monocytogenes*. This phenomenon is illustrated in panels A and B of FIG. 3. The total absence of any lysis plaque of the bacterial layer around the *Acanthamoeba castellanii* and *Hartmanella vermiformis* cysts is also noted, contrary to the phenomenon observed with *Willaertia magna*. All of these data and observations clearly show the predation effect of *Willaertia magna* toward the pathogenic bacterium *Listeria monocytogenes*.

LITERATURE REFERENCES

1. Akya A, Pointon A, and Thomas C. Viability of *Listeria monocytogenes* in coculture with *Acanthamoeba* spp, *FEMS Microbial Ecol* 70: 20-29, 2009.
2. Belessi C E, Gounadaki A S, Psomas A N, and Skandamis P N. Efficiency of different sanitation methods on *Listeria monocytogenes* biofilms formed under various environmental conditions. *Int J Food Microbial* 145 Suppl 1: S46-S2, 2011.
3. Bodennec J, Dey R, and Perron P. Novel method for biologically combating the proliferation of Legionella pneumophila, and novel disinfecting agent containing amoebic protozoa of the *Willaertia* genus, edited by University CBL, France: 2010,
4. Dijkstra R G. The occurence of *Listeria monocytogenes* in surface water of canals and lakes, in ditches of one big polder and in the effluents and canals of a sewage treatment plant, *Zentralbl Bakteriol Hyg[B]*176: 202-205, 1982.
5. Goulet V, Hedberg C, Le Monnier A, and de Valk H. Increasing incidence of listeriosis in France and other European countries. *Emerg Infect Dis* 14: 734-740, 2008,
6. Greub G, and Raoult D. Microorganisms resistant to free-living amoebae, *Clin Microbial Rev* 17: 413-433, 2004.
7. Khunkitti W, Lloyd D, Furr J R, and Russell A D. *Acanthamoeba castellanii*: growth, encystment, excystment and biocide susceptibility. *J Infect* 36; 41-48, 1998,
8. Lloyd D, Turner N A, Khunkitti W, Harm A C, Purr J R, and Russell A D. Encystation in *Acanthamoeba castellanii*: development of biocide resistance. *J Eukaryot Microbiol* 48; 11-16, 2001.
9. Ly TMC, and Miller H E. Ingested *Listeria monocytogenes* survive and multiply in protozoa, *J Med Mierobiol* 33: 51-54, 1990.
10. Mailles A, Lecuit M, Goulet V, Leclercq A, and Stahl J P. *Listeria monocytogenes* encephalitis in France. *Med Mal Infra* In Press.
11. Pushkareva VI, and Ermolaeva S A. *Listeria monocytogenes* virulence factor Listeriolysin O favors bacterial growth in co-culture, with the ciliate *Tetrahymena pyriformis*, causes protozoan encystment and promotes bacterial survival inside cysts, *BMC Microbiol* 10: 26, 2010.
12. Rajkovic A, Smigic N, Uyttendaele M, Medic H, de latter L, and Devlieghere F. Resistance of *Listeria monocytogenes, Escherichia coli* O157:H7 and *Campylobacter jejuni* after exposure to repetitive cycles of mild bactericidal treatments. *Food Microbiol* 26: 889-895, 2009.
13. Rakic-Martinez M, Drevets D A, Matta V. Katie V, and Kati S. *Listeria monocytogenes* strains selected on ciprofloxacin or the disinfectant benzalkonium chloride exhibit reduced susceptibility to ciprofloxacin, gentamicin, benzalkonium chloride and other toxic compounds. *Appl Environ Microbiot* In Press, 2011.
14. Thomas V, Bouchez T, Nicolas V. Robert S, Loret J F, and Levi Y. Amoebae in domestic water systems: resistance to disinfection treatments and implication in Legionella persistence. *J Appl Microbiol* 97: 950-963, 2004.
15. Weis J., and Seeliger HP. Incidence of *Listeria monocytogenes* in nature, *Appl Microbial* 30: 2932, 1975.
16. Zhou X, Elmose J, and Call DR. Interactions between the environmental pathogen *Listeria monocytogenes* and a free-living protozoan (*Acanthamoeba castellanii*). *Environ Micro biol* 9: 913-922, 2007.

The invention claimed is:

1. A method for controlling the proliferation of *Listeria monocytogenes* with the exception of the treatment methods applied to the human or animal body, comprising contacting the *Listeria monocytogenes* with a strain of amoebic protozoa of the species *Willaertia magna* deposited under number PTA 7824 or PTA 7825 at the ATCC.

2. The method as claimed in claim 1, characterized in that it is implemented for the disinfection of sanitation water or industrial water distribution networks, cooling circuits for industrial plants, or air-conditioning networks, or any industrial surfaces.

3. The method as claimed in claim 1, characterized in that it is implemented for controlling the information of biofilms in water pipes, or surfaces possibly in contact with human or animal food products.

4. A method for eliminating *Listeria* in water of liquids circulating in a pipe or network to be treated, comprising adding a protozoa corresponding to the strain deposited under number PTA 7824 at the ATCC or corresponding to the strain deposited under number PTA 7825 at the ATCC to said water or liquids.

5. The method of claim 4, characterized in that said *Listeria* are *Listeria monocytogenes*.

* * * * *